(12) United States Patent
Yager et al.

(10) Patent No.: US 7,655,443 B1
(45) Date of Patent: Feb. 2, 2010

(54) NUCLEIC ACID SEQUENCING WITH SIMULTANEOUS QUANTITATION

(75) Inventors: Thomas D Yager, Mississauga (CA); M Jason August, Toronto (CA)

(73) Assignee: Siemens Healthcare Diagnostics, Inc., Tarrytown, NY (US)

( * ) Notice: Subject to any disclaimer, the term of this patent is extended or adjusted under 35 U.S.C. 154(b) by 638 days.

(21) Appl. No.: 09/565,249

(22) Filed: May 5, 2000

Related U.S. Application Data

(60) Provisional application No. 60/133,168, filed on May 7, 1999.

(51) Int. Cl.
*C12P 19/34* (2006.01)
*C07H 21/04* (2006.01)
(52) U.S. Cl. .................. 435/91.2; 536/23.1; 536/24.33
(58) Field of Classification Search .............. 435/6, 435/91.1, 91.2, 183, 287.2, 810; 436/94; 536/23.1, 24.3, 24.33, 24.31
See application file for complete search history.

(56) References Cited

U.S. PATENT DOCUMENTS

| | | | | |
|---|---|---|---|---|
| 5,108,892 | A * | 4/1992 | Burke et al. | 435/6 |
| 5,219,727 | A * | 6/1993 | Wang et al. | 435/6 |
| 5,294,799 | A * | 3/1994 | Aslund et al. | 250/458.1 |
| 5,427,911 | A | 6/1995 | Ruano | |
| 5,476,774 | A * | 12/1995 | Wang et al. | 435/91.2 |
| 5,677,124 | A * | 10/1997 | DuBois et al. | 435/5 |
| 5,688,648 | A * | 11/1997 | Mathies et al. | 435/6 |
| 5,707,804 | A * | 1/1998 | Mathies et al. | 435/6 |
| 5,717,602 | A * | 2/1998 | Kenning | 700/266 |
| 5,756,455 | A * | 5/1998 | Kinzler et al. | 514/12 |
| 5,804,380 | A * | 9/1998 | Harley et al. | 435/6 |
| 5,830,657 | A * | 11/1998 | Leushner et al. | 435/6 |
| 5,858,671 | A * | 1/1999 | Jones | 435/6 |
| 5,866,336 | A * | 2/1999 | Nazarenko et al. | 435/6 |
| 5,888,736 | A * | 3/1999 | Lacroix et al. | 435/6 |
| 6,017,704 | A * | 1/2000 | Herman et al. | 435/6 |
| 6,063,608 | A * | 5/2000 | Kotewicz et al. | 435/194 |
| 6,190,889 | B1 * | 2/2001 | Jones | 435/91.1 |
| 6,265,193 | B1 * | 7/2001 | Brandis et al. | 435/194 |
| 6,287,801 | B1 * | 9/2001 | Bergsma et al. | 435/69.1 |
| 6,475,361 | B1 * | 11/2002 | Merenkova et al. | 204/451 |
| 2002/0046948 | A1 * | 4/2002 | Chow et al. | 204/450 |
| 2002/0119455 | A1 * | 8/2002 | Chan | 435/6 |
| 2002/0192669 | A1 * | 12/2002 | Sorge | 435/6 |

FOREIGN PATENT DOCUMENTS

WO    WO 98/41650 A2 *  9/1998
WO    WO 98/41650 A2 *  9/1998
WO    WO 9841650 A2 *  9/1998

OTHER PUBLICATIONS

Liu et al., "Rapid sequencing of unpurified PCR products by thermal asymetric PCR cycle sequencing using unlabeled sequencing primers," Nucleic Acids Research, 1993, vol. 21, No. 14, pp. 3333-3334.*
Salas-Solano et al., Analytical Chemistry, 1998, vol. 70, 1528-1535.*
Mansfield et al., "Fluorescent approaches to diagnosis of Lesch-Nyham syndrome and quantitative analysis of carrier status," Molecular and Cellular Probes, Aug. 1993, 7(4) 311-24.*
Holodniy et al., Journal of Clinical Investigation, Nov. 1991, vol. 88, pp. 1755-1759.*
Chow, Annals Academy of Medicine, Nov. 1997, vol. 26, No. 6, pp. 820-826.*
Mathies et al., Molecular and Cellular Probes,1993, vol. 17, pp. 311-324.*
Holodiny et al., Journal of Clinical Investigation, Nov. 1991, vol. 88, pp. 1755-1759.*
John W. Mellors, MD; Lawrence A. Kingsley, DRPH; Charles R. Rinaldo, Jr., PHD; John A. Todd, PHD; Brad S. Hoo, MS; Robert P. Kokka, DRPH; and Phalguni Gupta, Ph.D., Quantitation of HIV-1 RNA in Plasma Predicts Outcome after Seroconversion; 1995 American College of Physicians, Ann Intern Med. 1995; 122:573-579.

(Continued)

*Primary Examiner*—Bradley L Sisson
(74) *Attorney, Agent, or Firm*—Christopher L. Wight; Brinks Hofer Gilson & Lione

(57) ABSTRACT

Simultaneous sequencing and quantitation of a nucleic acid analyte in a sample using the same reagents for both assays is achieved by processing a sample containing, or suspected of containing the nucleic acid analyte of interest using a single set of reagents through a plurality of thermocycles to obtain a mixture of labeled polynucleotides which are used for the determination of both sequence information about the target nucleic acid and the amount of target nucleic acid present in the sample. The fragments are separated on the basis of size, for example by electrophoresis, and the label associated with the separated fragments is detected. The positions of the separated nucleic acid fragments are evaluated to obtain information about the sequence of the target nucleic acid analyte, and the intensity of a signal derived from the label associated with one or more of the separated fragments is evaluated to determine the quantity of the target nucleic acid analyte in the sample. Only one label is needed for both sequencing and quantitation, although two or more labels may be used if bidirectional sequencing is concurrently performed.

14 Claims, 10 Drawing Sheets

OTHER PUBLICATIONS

J. Cuzick, G. Terry, L. Ho, T. Hollingworth & M. Anderson; Type-specific human papillomavirus DNA in abnormal smears as a predictor of high-grade cervical intraepithelial neoplasia; Br. J. Cancer 69:167-171.

P.J. Bavin, J.A. Giles, A. Deery, J. Crow, P.D. Griffiths, V.C. Emery & P.G. Walker, Use of semi-quantitative PCR for human papillomavirus DNA type 16 to identify women with high grade cervical disease in a population presenting with a mildy dyskaryotic smear report. B. J. Cancer (1993) 67, 602-605.

J. Mulder, N. McKinney, C. Christopherson, J. Sninsky, L. Greenfield and S. Kwok; Rapid and Simple PCR Assay for Quantitation of Human Immunodeficiency Virus Type 1 RNA in Plaxma: Application to Acute Retroviral Infection; Journal of Clinical Microbiology, Feb. 1994, p. 292-300, vol. 32, No. 2.

Robin L. Dewar, Helene C. Highbarger, Marinella D. Sarmiento, Hohn A. Todd, M. B. Vasudevachari, Richard T. Davey, Jr., Joseph A. Kovacs, Norman P. Salzman, H. Clifford Lane, and Mickey S. Urdea; Application of Branched DNA Signal Amplification to Monitor Human Immunodeficiency Virus Type 1 Burden in Human Plasma: The Journal of Infectious Diseases 1994; 170:1172-9.

Bob Van Gemen, Tim Kievits, Rianne Schukkink, Dianne Van Strijp, Lawrence T. Malek, Roy Sooknanan, Han G. Huisman and Peter Lens, Quantification of HIV-1 RNA in plasma using NASBA during HIV-1 primary infection; Journal of Virological Methods, 43 (1993) 177-188.

Cycle Sequencing, Keith Kretz, et al. Stratagene Cloning Systems, LaJolla, CA, PCR Methods and Applications 3:S107-S112 (1994).

* cited by examiner

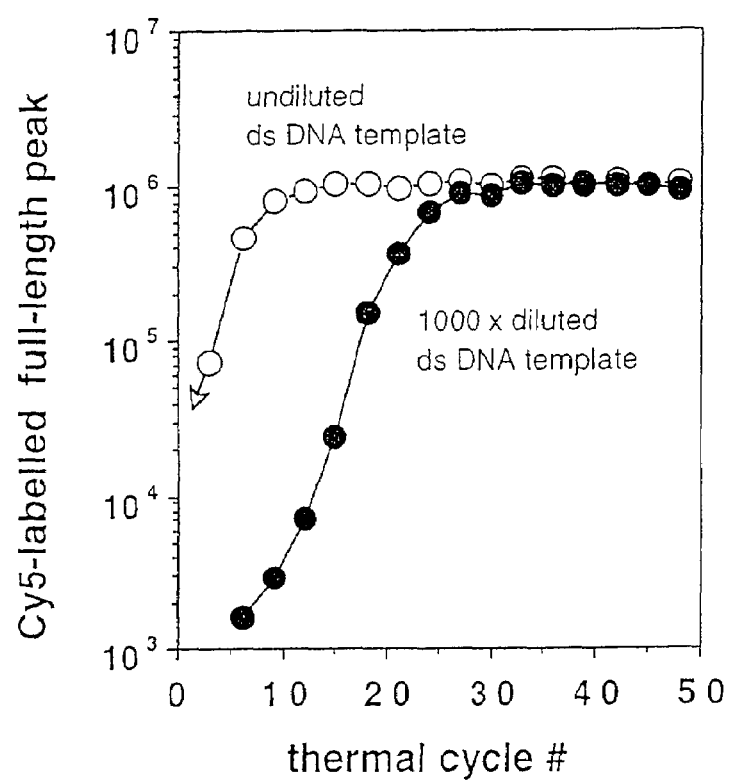
FIG. 5-A

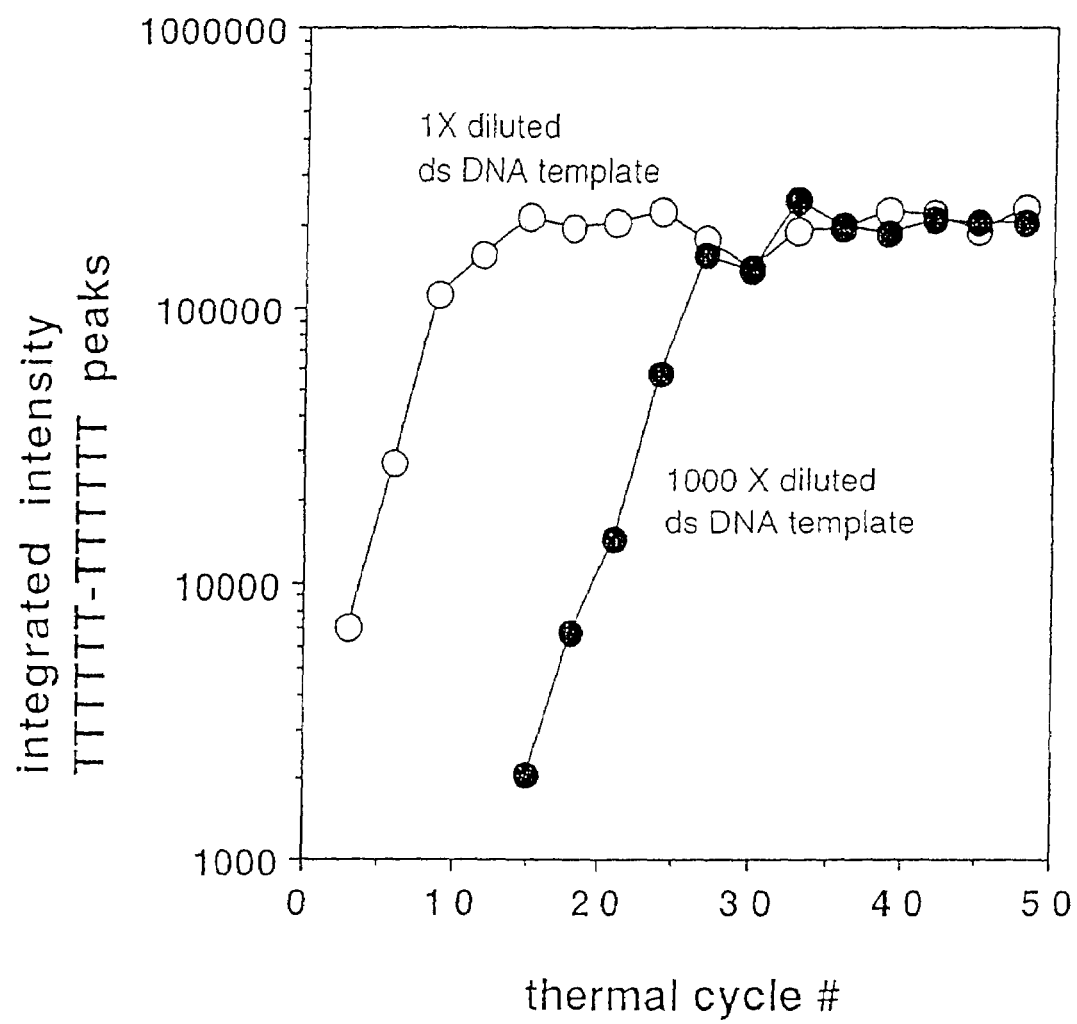
FIG. 5-B

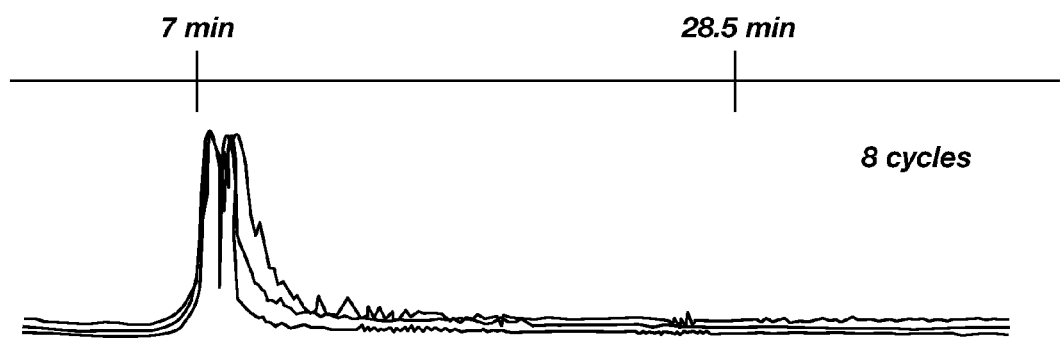
FIG. 7-A
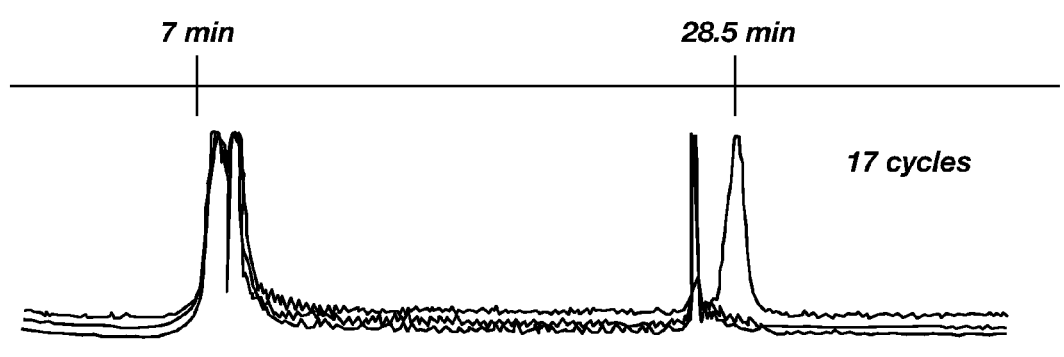
FIG. 7-B
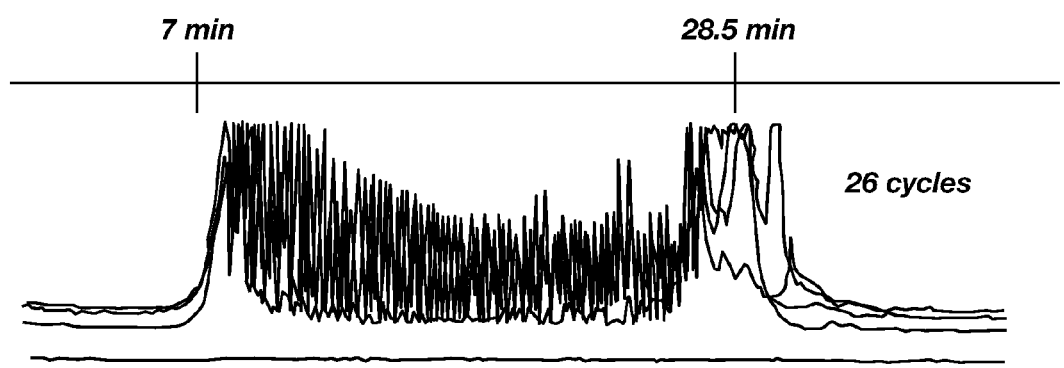
FIG. 7-C
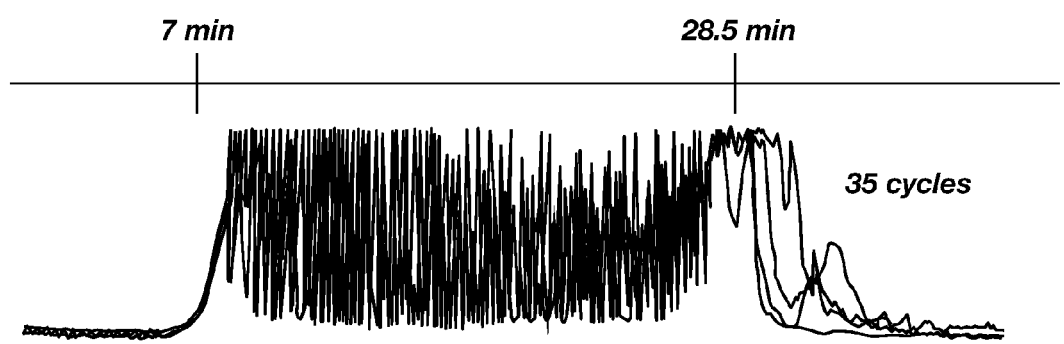
FIG. 7-D

NUCLEIC ACID SEQUENCING WITH SIMULTANEOUS QUANTITATION

This application claims priority from U.S. Provisional Application No. 60/133,168 filed May 7, 1999, which is incorporated herein by reference.

FIELD OF THE INVENTION

This application relates to a method and kit for the simultaneous sequencing and quantitation of a nucleic acid analyte in a sample.

BACKGROUND OF THE INVENTION

Academic and commercial interest in nucleic acid diagnostics has, to date, focused on qualitative assays. This type of assay determines the presence or absence in a patient sample of a specific gene mutation or infectious pathogen. Molecular assays which achieve these goals are well known. Many rely on amplification techniques, known to those skilled in the art such as the polymerase chain reaction (PCR), NASBA or 3SR, with or without hybridization probing. Others such as Digene Hybrid Capture Assays (DiGene Diagnostics Inc.) do not require amplification prior to detection and are generally less sensitive. Assays have been developed for many infectious pathogens such as *Chlamydia trachomatis*, Human Immunodeficiency Virus Type 1 (HIV-1) and Type 2 (HIV-2), and human papilloma virus (HPV). Some of these tests have been launched commercially by Roche Diagnostic Systems, Abbott Laboratories and others.

Quantitative assays of nucleic acid analytes also prove useful in diagnosis of a variety of medical disorders. For example, viral load in HIV infection may be correlated with increased risk of clinical progression of HIV disease (Mellors. J. W. et al. (1995). Quantitation of HIV-1 RNA in plasma predicts outcome after seroconversion. Ann. Intern. Med. 122: 573-579). While this example is best known, other quantitative applications also have clinical and commercial interest, such as quantitation of human papilloma virus in PAP smears. (Cuzick, J. et al. (1994) Type-specific human papillomavirus DNA in abnormal smears as a predictor of high-grade cervical intraepithelial neoplasia. Br. J. Cancer 69:167-171; Bavin P. J. et al. (1993) Use of semi-quantitative PCR for human papillomavirus DNA type 16 to identify women with high grade cervical disease in a population presenting with a mildly dyskaryotic smear report. Br. J. Cancer 67:602-605.)).

Notwithstanding their usefulness, quantitative assays of nucleic acid analytes have lagged behind in development. The delay may in part be attributed to technology barriers. Most instruments and methods provide inadequate dynamic range for measuring quantities, thus requiring labor intensive techniques such as multiple serial dilutions and repeat reactions. Further, until recently, PCR methods have been perceived as unreliable for quantitation due to the possibility of contamination and non-linear enzyme kinetics.

The AMPLICOR HIV-1 MONITOR® (Roche Molecular Systems) test is a quantitative molecular assay for HIV RNA levels in blood. The assay is performed on HIV-1 and a subset of HIV-2 RNA found in 200 uL of blood plasma. The RNA is purified from the plasma sample, reverse transcribed and amplified by PCR. The reaction products are quantified by a probe based photometric assay and compared to the levels of a control RNA of known quantity that is added to the plasma sample. The control RNA is reverse transcribed along with the sample RNA and co-amplified using the same amplification primers. Six serial dilutions are necessary to detect across the full range of detectable viral load: 400 copies to 750,000 copies per ml. The test requires that for samples over 750,000 copies, (over 2.2 million copies per ml have been detected) the original patient sample must be diluted. The AMPLICOR assay therefore quantifies across the full range of possible values by a series of multiple dilutions. The AMPLICOR assay does not determine which sub-type or sub-types of HIV-1 are present, and it does not establish if HIV-2 was amplified.

Other quantitative HIV assays have been reported. Some of these papers include:

Mulder, J et al. Rapid and simple PCR assay for quantitation of human immunodeficiency virus type 1 RNA in plasma: Application to acute retroviral infection. J. Clin. Micro. 32:292-300

Dewar, R. L. et al, 1994 Application of branched DNA signal amplification to monitor human immunodeficiency virus type 1 burden in human plasma. J. Infect. Dis. 170:1172-1179 van Gemen, B. et al. 1993 Quantitation of HIV-1-1 RNA in plasma using NASBA during HIV-1-1 primary infection. J. Vir. Meth. 43:177-188.

Each of these prior methods would require the performance of a separate set of reactions for quantitation and sequencing, and even if these methods could be performed concurrently in a single vessel the need for multiple reaction increases the number of reagents required and thus the cost of the procedure.

WO98/41650 discloses a method for quantitative and qualitative analysis of a nucleic acid analyte in a sample suspected to contain the nucleic acid analyte. The method comprises the steps of:

(a) combining the sample with a control nucleic acid, and two primer pairs,
  a first primer pair effective to amplify a conserved region of the nucleic acid analyte if present in the sample to produce a conserved fragment having a first length and to amplify the control nucleic acid to produce a control fragment having a second length different from the first length, one member of the first primer pair being labeled with a detectable label, and
  a second primer pair effective to amplify a second region of the nucleic acid analyte to produce a sequencing fragment, one member of the second primer pair being labeled with a label effective to permit capture of the primer;

(b) amplifying the sample and control nucleic acid using the first and second primer pairs to produce an amplification product mixture containing conserved fragments, sequencing fragments and control fragments when the nucleic acid analyte is present in the sample, and only control fragment when the nucleic acid analyte is not present in the sample;

(c) analyzing the relative amounts of conserved fragments and control fragments in the amplification product mixture to quantify the amount of nucleic acid analyte in the sample; and (d) determining the sequence of the sequencing fragment in the amplification mixture to determine the qualitative characteristics of any nucleic acid analyte in the sample. Thus, although the methodology of WO98/41650 permits sequencing and quantitation in a common reaction, it utilizes different primer pairs for the generation of products evaluated for sequencing and quantitation.

SUMMARY OF THE INVENTION

The present invention provides a methodology and associated kits for simultaneous sequencing and quantitation of a nucleic acid analyte in a sample using the same reagents for both assays. In accordance with the invention, a sample containing, or suspected of containing the nucleic acid analyte of interest is processed using a single set of reagents through a plurality of thermocycles to obtain a mixture of labeled polynucleotides which are used for the determination of both sequence information about the target nucleic acid and the amount of target nucleic acid present in the sample. The fragments are separated on the basis of size, for example by electrophoresis, and the label associated with the separated fragments is detected. The positions of the separated nucleic acid fragments are evaluated to obtain information about the sequence of the target nucleic acid analyte, and the intensity of a signal derived from the label associated with one or more of the separated fragments is evaluated to determine the quantity of the target nucleic acid analyte in the sample. In accordance with the invention, only one label is needed for both sequencing and quantitation, although two or more labels may be used if bidirectional sequencing is concurrently performed.

BRIEF DESCRIPTION OF THE DRAWINGS

FIGS. 5A and 5B show the relationship between signal intensity and number of CLIP cycles for the full length peak and sequencing fragment peaks, respectively;

FIGS. 7A-D show raw data traces obtained for aliquots taken after varying numbers of CLIP cycles;

DETAILED DESCRIPTION OF THE INVENTION

Figure 1:
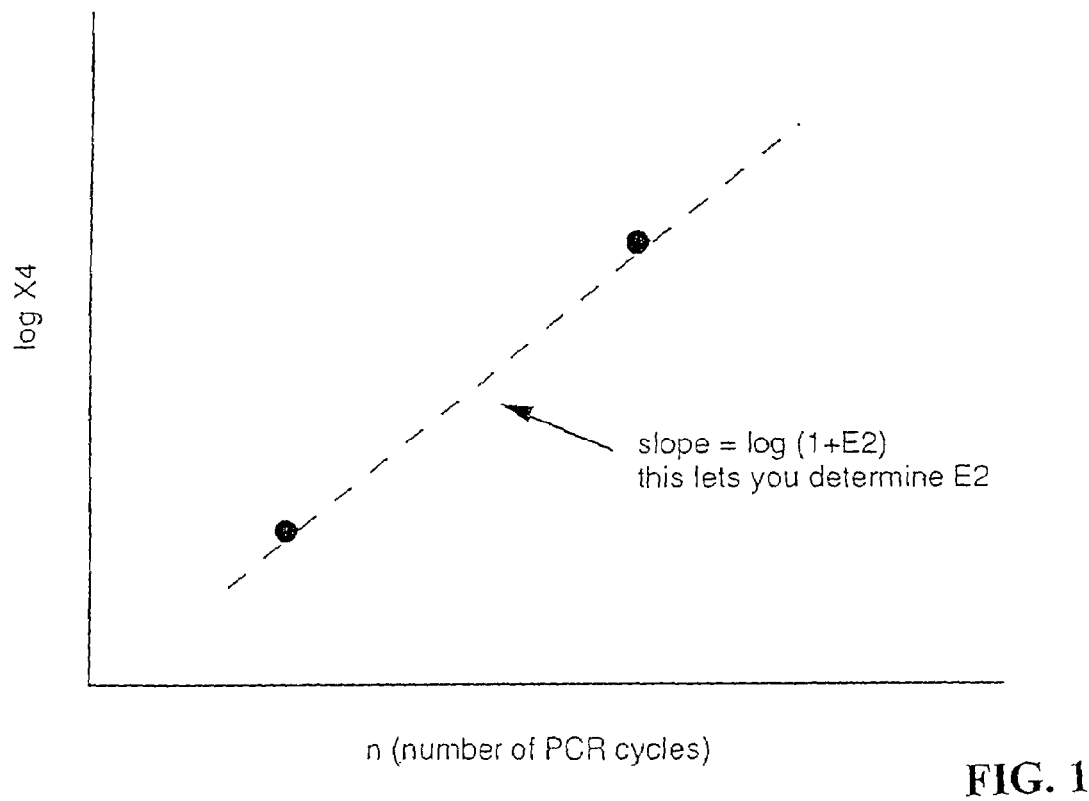
FIG. 1 is a calibration plot for the determination of the efficiency of PCR, $E_2$.

The present application can be utilized in the analysis of either DNA or RNA analytes, and is particularly useful for the simultaneous determination of microbial (bacterial or viral) type and load. As discussed below, one particular application for the invention is in the simultaneous genotyping and viral load determination for HIV-1.

In accordance with the invention, a sample containing or suspected of containing a target nucleic acid is processed using a single set of reagents to produce labeled polynucleotides which are used for the determination of both sequence information about the target nucleic acid and the amount of target nucleic acid present in the sample. As used herein, the phrase "a single set of reagents" means that the same reagents are used to produce the fragments of nucleic acid that are used to convey information about both the amount and sequence of the target nucleic acid. It does not preclude the use of multiple sets of primers in different steps to generate these fragments (for example nested PCR and sequencing fragments) nor does it preclude the use of a different set of primers for the creation of fragments from an internal standard sequence or a calibration sequence. The use of a single set of reagents also encompasses the use of this same set of reagents in each of two or more parallel replicate reactions conducted in different vessels.

The invention can be practiced in several variations. First, the invention may be practiced such that the same fragments (i.e., sequencing fragments) are evaluated for both determinations. Second the invention may be practiced such that different fragments or groups of fragments produced by reaction with the single set of reagents are used for the two determinations, for example, sequencing fragments for the determination of sequence information and a full-length peak (from coupled amplification and sequencing or CLIP) for the determination of the amount of target nucleic acid. Within this second alternative there are further variations. The different fragments or groups of fragments may be produced in parallel replicate reactions with the same reagents in each tube, or they may be produced in a single tube. Furthermore, while the fragments used to determine the sequence information and the amount of target nucleic acid are all generated as a result of the a single set of reagents, it is not required that they have been subjected to the same number of thermal cycles. Thus, in the first case, the number of thermal cycles used in the creation of the fragments may be different between the two tubes. In the second case, an aliquot may be removed from the reaction mixture for use in the determination of the amount of target nucleic acid at an intermediate stage of the reaction, with additional thermal cycles being performed subsequently to produce fragments for determination of sequence information.

Besides these variations, the method of the invention may include additional steps, depending on the nature of the sample and on the nature of the chemistry employed to produce the polynucleotide fragments. Thus, in accordance with one embodiment of the invention, the sample is first processed through one or more steps which increase the amount of target nucleic acid present in the sample. By way of example, an RNA sample (for example an HIV-1 RNA from a human AIDS patient) is subjected to an RT-PCR procedure, in which reverse transcription is used to make a $1^{st}$ strand cDNA copy of the RNA, and the cDNA copy is then amplified by PCR. DNA samples, on the other hand, could be amplified directly by PCR, or other amplification techniques, including LCR (ligase chain reaction) and the like.

After the increase in the amount of the DNA, the DNA is processed to generate Sanger-type sequencing fragments, incorporating a detectable label, using a single set of reagents. A preferred label type is a fluorescent label, although radiolabels, chromophoric labels, or chromogenic or fluorogenic labels can also be used. The method for producing the sequencing fragments may be cycle sequencing as described in Kretz et al., in *PCR Methods and Applications* 3: S107-S112 (1994) or coupled amplification and sequencing (CAS) as described in U.S. Pat. No. 5,427,911. These processes produce fragments which can be analyzed to determine both the amount of target nucleic acid and sequence information about the target nucleic acid. In the case of cycle sequencing, a full-length product may not be generated in sufficient amount for quantitation. Thus, if cycle sequencing is used to generate the fragments, the sequencing peaks are used directly for determination of the amount of the target nucleic acid in the sample.

The prior step of increasing the amount of nucleic acid in the sample is not necessary, however, since it is possible to generate fragments in a single step process using a single set of reagents. Such a process is described in U.S. Pat. Nos. 5,830,657 and 5,888,736, and is referred to herein by the assignee's trademark for this procedure, CLIP. This type of reaction can be used independently (in which case it plays the part of both types of steps) or in combination with a distinct step for increasing the amount of nucleic acid analyte in the sample. In the CLIP reaction, the sample is combined with forward and reverse primers flanking the region of interest, a thermally stable polymerase with low discrimination between deoxy and dideoxynucleoside triphosphates, deoxynucleoside triphosphates and one species of dideoxynucleoside triphosphate. This reaction mixture is cycled through multiple thermocycles to create fragments terminated with the dideoxy nucleoside.

An important characteristic of the processing step or steps used to generate the polynucleotide fragments is that they be performed in the "quantitative regime." It is known in the art that cyclic processes may decrease in efficiency after a number of cycles, such that the amount of product from one cycle to the next ceases to be directly related in a simple and predictable fashion to the amount of product in the preceding cycle. Thus, for example, in a PCR amplification, in the first cycle the amount of product after the first cycle is essentially 2 times the amount of starting material, after the second cycle it is essentially 4 times, then 8 times and so forth. At some number of cycles, however, the amount of product is less than would be predicted according to a simple exponential growth model. The present invention should be performed at lower cycle numbers where this decrease in efficiency is not observed, and where a plot of log of the amount of product as a function of cycle number is linear. This is referred to in the specification and claims as being "within a quantitative regime."

In order to maintain the reaction within a quantitative regime, it may be desirable to take an aliquot of sample for determination of the amount of nucleic acid analyte, and then continue for additional cycles of the reaction generating sequencing fragments to produce the final mixture that will be used in sequence analysis. For example, as discussed in greater detail below, it has been determined that in the CLIP reaction the product produced in the first 20 cycles is predominantly the full-length product, while in subsequent cycles (for example 25-40) the amount of full-length product has reached a plateau and the sequencing fragments increase in number. If the full length product is to be used for quantitation, it is desirable to take an aliquot after about 20 cycles for this purpose, and then continue for additional cycles to generate sequencing ladders.

After the fragments are generated, they are separated by size, for example by electrophoresis, and detected using an apparatus appropriate to the type of label. The intensity of the sequencing peaks may be evaluated as a measure of the amount of nucleic acid analyte in the sample. The "intensity" utilized may be based on any reproducible parameter which reflects the intensity of the signal from a given peak, such as the height or area of the peaks. The "intensity" may be determined based on a representative peak (such as the full length peak) or it may be determined based on an average or total of individual peak heights over a predetermined window. This intensity is correlated to the amount of nucleic acid which was produced in the sequencing reaction, which is in turn correlated to the amount of nucleic acid analyte which was present in the initial sample. Intensities of the full length peak and terminated sequencing fragment peak(s) can be used independently to provide confirmatory measures of the amount of target nucleic acid in the sample.

The sequencing fragments in the modified sample are also used for the determination of information about the sequence of the target nucleic acid analyte in accordance with techniques well-known in the art. Thus, the present invention provides a method for the simultaneous sequencing and quantitation of a target nucleic acid analyte in a sample using a single set of reagents, optionally in a single vessel.

The method of the invention is suitably practiced using a kit which is specifically adapted for use in the method. For a given target nucleic acid, the kit may contain at least a primer pair flanking a region of analytical interest within the target nucleic acid, a thermostable template-dependent DNA polymerase, feedstock solutions and buffers for performing a thermally-cycled primer extension reaction, and calibration information specific to the production lot of reagents within the kit. The calibration information may be in the form of numerical efficiency parameters or calibration curves provided in print on packaging or product inserts accompanying the kit. The calibration information may also be in machine-readable format, for example a diskette or compact disk. Alternatively, the calibration information may be provided indirectly, by packaging with the kit the instructions (and a password/user code if desired) for obtaining calibration information from an on-line source such as an web site or an ftp site.

Additional components may be included in the kit to provide the complete chemistry for the method to be performed. Thus, for purposes of analyzing RNA targets, the kit also includes a reverse transcriptase and the corresponding calibration information. Where the methodology employed utilizes a separate amplification step, the kit includes appropriate reagents (such as PCR primers which flank the primers for generating the final sequencing fragments) and corresponding calibration information.

A kit for quantitation and sequencing of a target nucleic acid analyte with an internal standard does not need reagent-specific calibration information. In this case, the kit includes the reagent components listed above, plus a reference polynucleotide, which may be provided in pre-measured amounts, and primers (including at least one labeled primer) for carrying out coprocessing of the reference polynucleotide with the sample. When a two step process involving PCR amplification followed by generation of terminated sequencing fragments is employed, the reference polynucleotide and the sample are preferably amplified by the same primers to produce an amplification product of substantially equal length. In addition, although the primers for generation of sequencing fragments are different, and are labeled with distinguishable labels, they preferably produce full-length products of equal, or at least substantially equal length. Selection of such primers is desirable to eliminate or minimize any differential amplification that may arise from different template lengths. Also, the reference polynucleotide preferably has a substantially similar composition and sequence to the target nucleic acid analyte, to eliminate or minimize any differential amplification that may arise from differences in template composition or sequence.

In the following explanation the sequencing fragments are assumed to be generated in a CLIP reaction. It will, however, be appreciated that other types of sequencing reactions could also be utilized, without departing from the invention. Further, this discussion assumes an initial RNA sample and thus includes a discussion of RT efficiency which would of course be irrelevant to a DNA analyte. In addition, while the following discussion refers to the separate determination of efficiencies for each step of the reaction and the application of these efficiencies individually to the experimental peak size, an overall efficiency could also be determined and applied to the experimental peak size to arrive at a quantitation of the amount of nucleic acid analyte sequenced.

The following specific discussion and examples are provided to provide a more complete understanding of the invention, and are not intended as limitations on the scope of the invention as described generally above

EXAMPLE 1

The amount of an RNA target nucleic acid analyte in a sample can be determined from the intensity of a sequencing reaction peak or peaks as follows. The sample contains an initial molar amount $X_1$ of the RNA target. By reverse transcription, this is converted into an molar amount $X_2$ of full-length first-strand cDNA. This conversion process has an efficiency $E_1$, where $0 \leq E_1 \leq 1$. Thus, $$X_2 = E_1 X_1.$$

The molar amount $X_2$ of the first-strand cDNA is passed into a PCR reaction for n cycles, each with an efficiency $E_2$, where $0 \leq E_2 \leq 1$. The PCR is performed within a quantitative regime so that $E_2$ is constant across cycles. This produces a molar amount $X_3$ of double-stranded PCR product:

$$X_3 = X_2(1+E_2)^n.$$

The molar amount $X_3$ of double-stranded PCR product is passed into a CLIP reaction for m cycles, each with an efficiency $E_3$, where $0 \leq E_3 \leq 1$. Again, CLIP is performed in a quantitative regime so that $E_3$ is constant across cycles. This produces a molar amount $X_4$ of CLIP product, $$X_4 = X_3(1+E_3)^m.$$

These equations are combined to obtain an expression which relates the amount of CLIP product ($X_4$, a measured quantity) to the initial amount of RNA template present in the sample ($X_1$, the unknown we would like to determine) as follows:

$$X_4(E_1X_1)(1+E_2)^n(1+E_3)^m.$$

This equation can be transformed to a logarithmic form:

$$\log(X_4) = \log(X_1 E_1) + n(\log(1+E_2)) + m(\log(1+E_3)).$$

The equations for $X_4$ and $\log(X_4)$ describe a monotonically-increasing function, $X_4 = f(X_1)$ with five parameters ($E_1$, $E_2$, $E_3$, n and m). The number of PCR cycles (n) and the number of CLIP cycles (m) are fixed by the analyst performing the assay. Therefore, three calibration runs to establish $E_1$, $E_2$ and $E_3$ should make these equations determinant.

The first calibration run is performed to determine the efficiency of the PCR reaction, $E_2$. In this calibration, samples prepared after different numbers of PCR cycles (n) are processed with a fixed amount of DNA template and a fixed number of CLIP cycles to produce measured amounts of CLIP product. The results are plotted in a semilog plot of $X_4$ (CLIP product) versus n as shown in FIG. 1. The slope of the line is equal to $\log(1+E_2)$ which allows the determination of a value of $E_2$.

Figure 2:
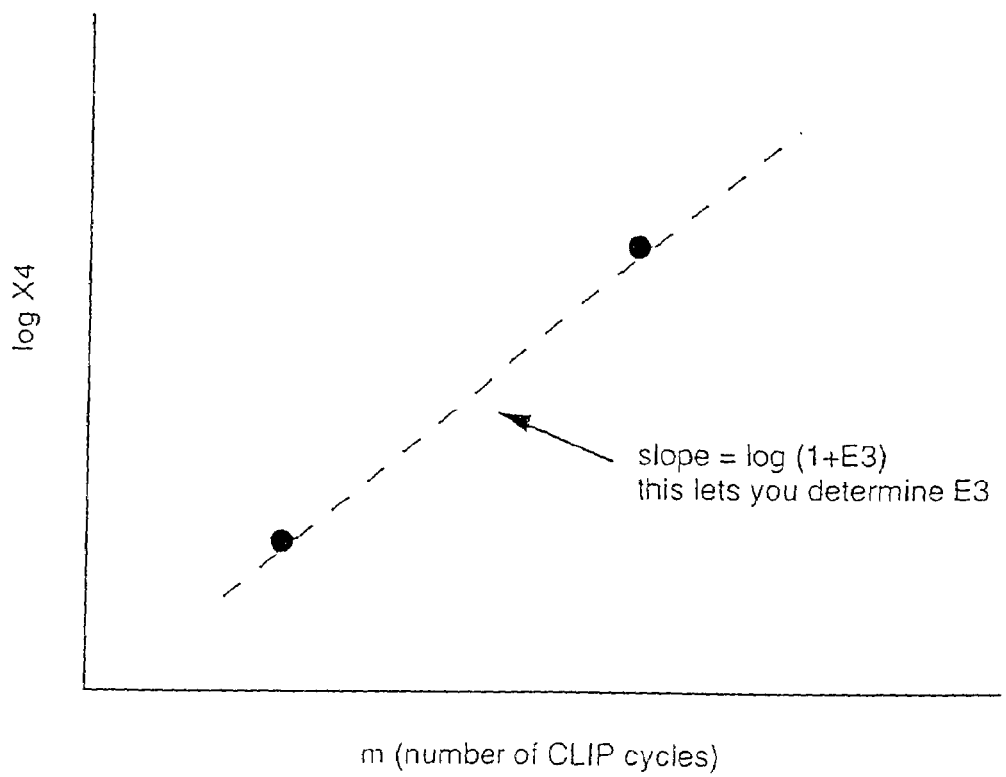
FIG. 2 is a calibration plot for the determination of the efficiency of CLIP, $E_3$.

The second calibration run is performed to determine the efficiency of the CLIP reaction, $E_3$. In this calibration, samples prepared with a fixed amount of DNA template and a fixed number of PCR cycles are subjected to differing numbers of CLIP cycles to produce measured amounts of CLIP product. The results are plotted in a semilog plot of $X_4$ (CLIP product) versus m as shown in FIG. 2. The slope of the line is equal to $\log(1+E_3)$ which allows the determination of a value of $E_3$.

Figure 3:
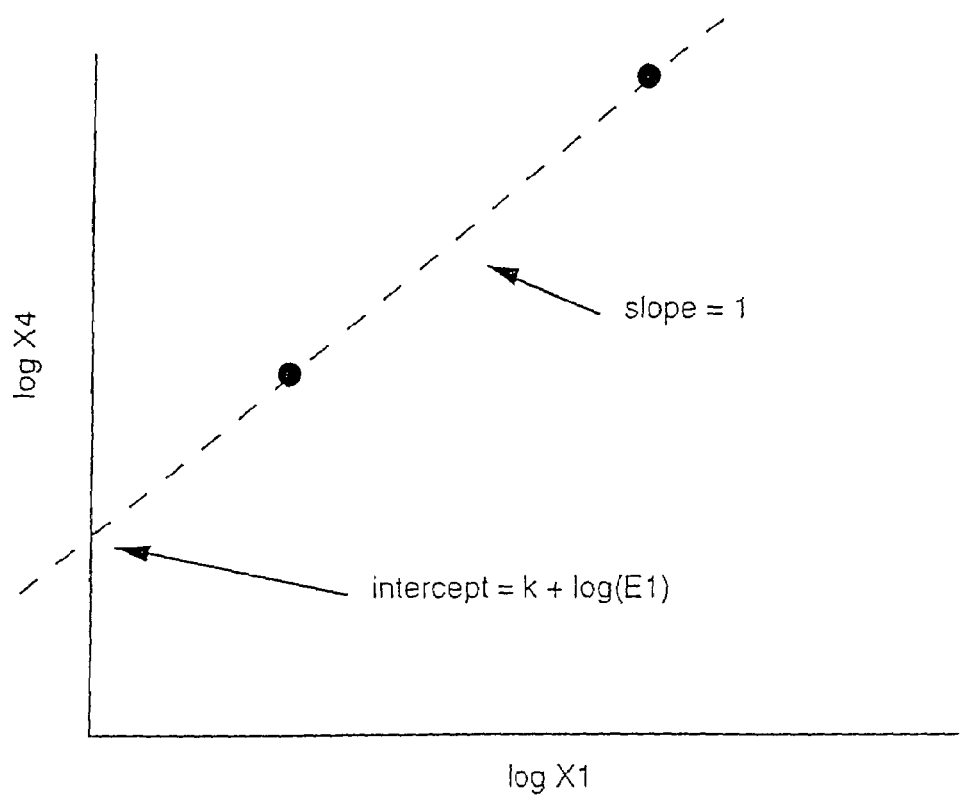
FIG. 3 is a calibration plot for the determination of the efficiency of reverse transcription (RT), $E_1$.

To determine the efficiency $E_1$ of the RT reaction, we first rewrite the equation as follows:

$$\log(X_4) = k + \log(X_1) + \log(E_1)$$

where the constant $k = n(\log(1+E_2)) + m(\log(1+E_3))$. A third calibration experiment is done in which samples containing varying amounts of RNA template are processed for a fixed number of PCR cycles and a fixed number of CLIP cycles. A log-log plot of the measured amount of product ($X_4$) versus the known amount of RNA template ($X_1$) has a slope of 1 and an intercept equal to $k + \log(E_1)$ as shown in FIG. 3. Since k can be calculated from the previous calibrations and known values, the value of $E_1$ can be determined from the intercept.

The three efficiency parameters, $E_1$, $E_2$ and $E_3$ may be determined for each batch of reagents packaged into kit format. In this case, the efficiency parameters are supplied (in the form of a calibration sheet or other format for providing calibration information) with each kit containing reagents from a particular production run, and can be used to generate performance curves through the expiry date of the kit. Alternatively, the kit can contain all of the reagents and instructions for the user to perform and determine kit-specific efficiency parameters in accordance with the invention.

EXAMPLE 2

Figure 4:
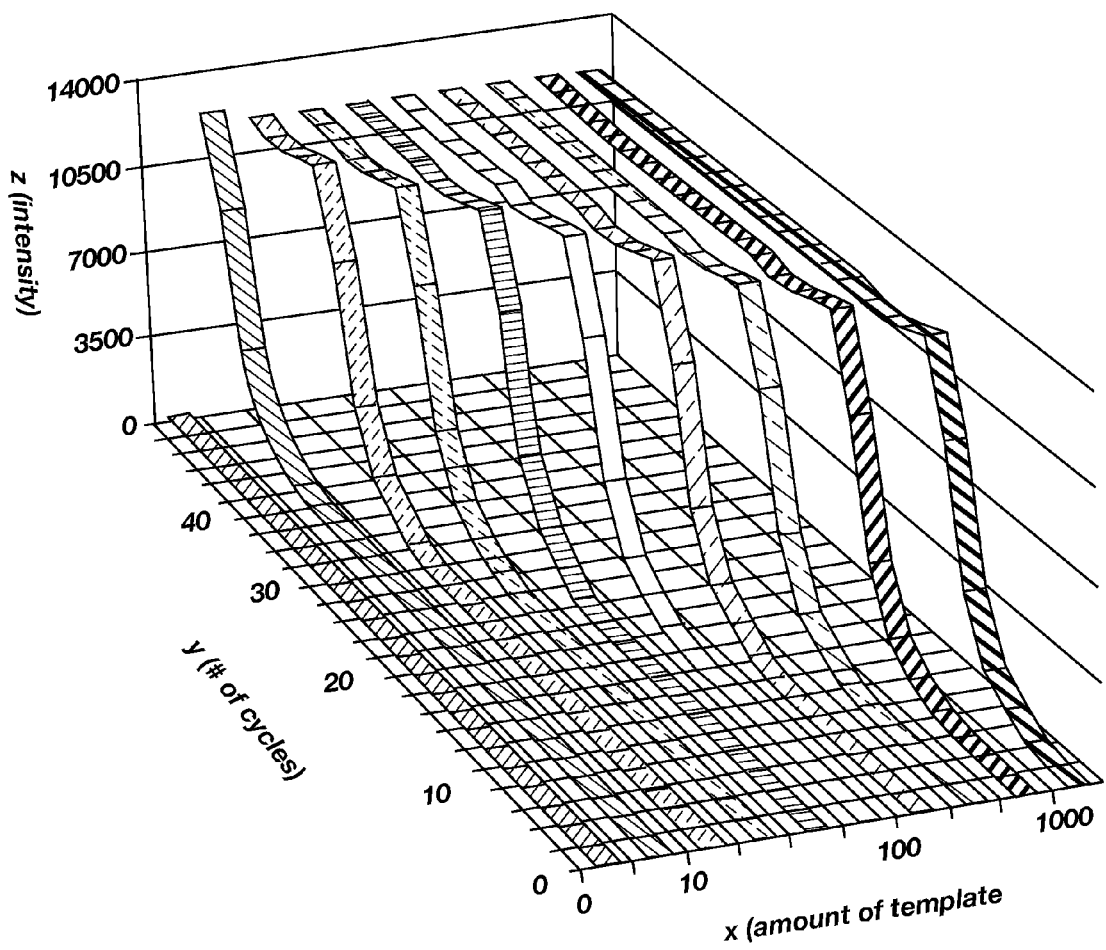
FIG. 4 is a set of curves describing the overall efficiency of an RT-PCR process.

As an alternative to the individual determination of the efficiency parameters, the overall efficiency of the conversion of starting template to product (sequencing fragments) may be considered. In this case, an empirical set of performance curves may be generated for each production run of reagents in a kit. These curves describe the overall efficiency of the sequencing and quantitation process under various operating conditions. An example is shown in FIG. 4. In this multidimensional plot, the x-axis is the amount of template ($X_1$), the y-axis is the number of CLIP cycles (m) and the z-axis is the measured amount of product (X4). As can be seen, increasing amounts of template produce curves with an inflection point at decreasing numbers of CLIP cycles. Therefore, if the number of CLIP cycles (m) is known, the amount of template ($X_1$) can be inferred from the shape of the product intensity curve ($X_4$) versus CLIP cycles (m).

EXAMPLE 3

A double stranded HIV-1 amplicon was subjected to quantitative CLIP, both in undiluted form and at a 1000-fold dilution. The undiluted sample produced a high intensity signal in both the full-length CLIP portion, and also in the CLIP sequencing ladder after CLIP cycle number 12. Over this number of cycles, the 1000× dilution produced a much less intense signal for both the full length product and the sequencing ladder. For the diluted sample, approximately 27 CLIP cycles were required to obtain the similar signal intensities.

There is a quantitative relationship between template concentration and intensity of the CLIP products. This can be seen clearly by graphing signal intensity as a function of CLIP cycle number. FIG. 5A shows such a plot for the full length peak observed for the undiluted and diluted samples described above. FIG. 5B shows a comparable plot for dideoxy-terminated peaks in a T-rich region at positions 204-252.

EXAMPLE 4

Figure 6:
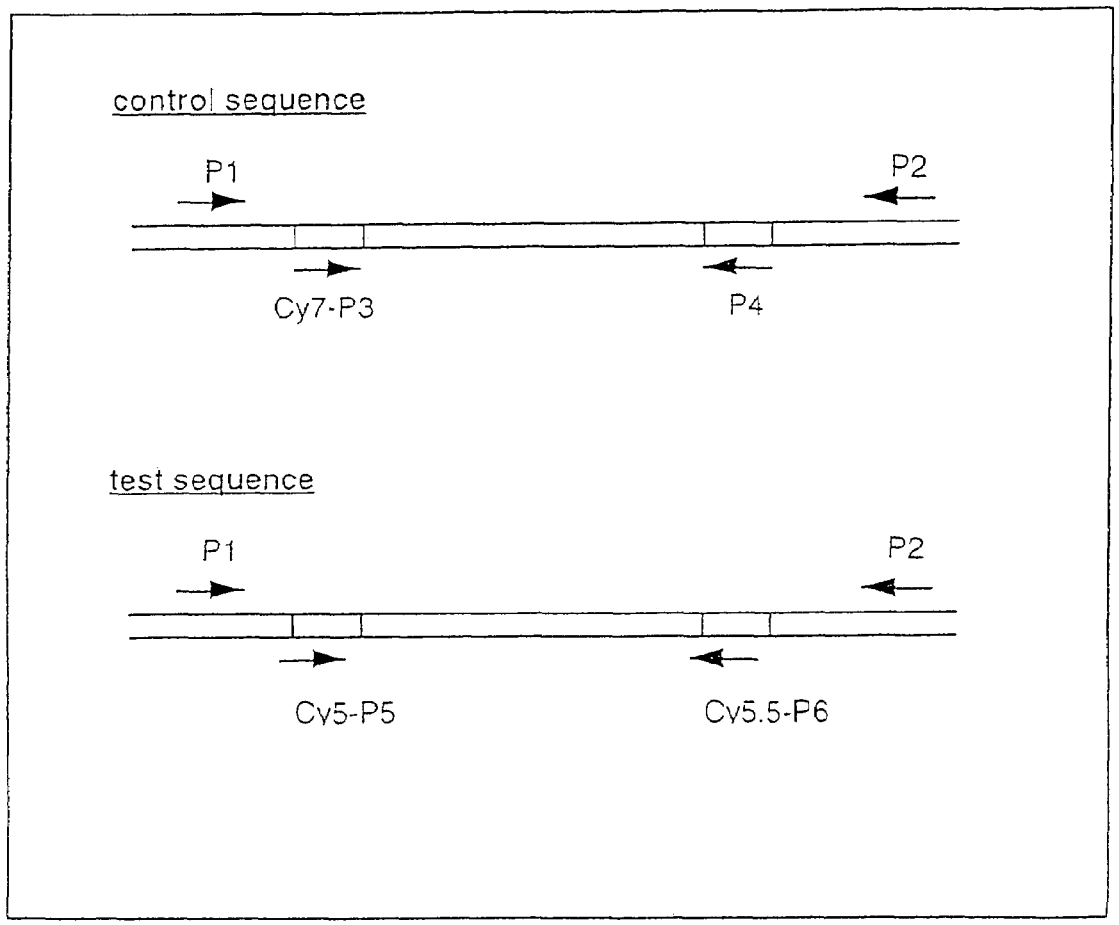
FIG. 6 shows primer positions for a three-dye scheme for analysis of a test sequence using an internal standard.

The invention may also be configured to use an internal standard to achieve absolute calibration. The internal standard is coprocessed in the same reaction to produce polynucleotide sequencing fragments having a distinctive dye as a label. For example as illustrated in FIG. 6, two DNA templates which have identical PCR priming sites ($P_1$ and $P_2$) but different CLIP priming sites ($P_3$ and $P_4$ in the internal standard sequence, $P_5$ and $P_6$ in the test sequence) can be used. Preferably, the length $|P_2-P_1|$ should be the same in the two templates. Also, the length $|P_4-P_3|$ should equal the length $|P_6-P_5|$ to eliminate any differential amplification in PCR or CLIP that arises from different template lengths. The templates are simultaneously coamplified by PCR using primers $P_1$ and $P_2$. Two independent, but simultaneous CLIP reactions are then performed in the same tube. One reaction produces sequencing fragments from the internal standard sequence using primers $P_3$ and $P_4$. The other produces sequencing fragments from the test sequence using primers $P_5$ and $P_6$. Also, the primers pairs ($P_3/P_4$ and $P_5/P_6$) preferably have comparable thermodynamic binding properties (Tm's) for their targets. Suitably, one of the primers for the internal standard sequence and both primers for the test sequence are labeled with distinctive labels, such as CY5, CY5.5 and CY7 as shown in order to achieve both quantitation and bidirectional sequencing of the target molecule in the same reaction. Since the amount of control sample added in the first instance is known, the intensity of the control peak (adjusted for differences in excitation efficiency and instrumental detection efficiency), provides an absolute calibration against which signal intensity of the peaks derived from the test sequence can be measured.

To demonstrate the sequence accuracy of performing two simultaneous CLIP reactions to obtain sequence information in a single tube, two templates and two sets of CLIP primers were combined. Template 1 was a 1274 bp HIV RT-PCR product sequenced using an unlabeled forward primer and a CY5-labeled reverse primer. Template 2 was a 330 bp segment of HLA DRB1 gene, sequenced using an M13 CY5.5-labeled forward primer and an unlabeled reverse primer. The templates and primers were combined with AmpliTaq FS polymerase, terminating dideoxy and non-terminating deoxynucleoside triphosphates and cycled through multiple thermal cycles (60° C. annealing temperature). After the CLIP reaction, the reaction products were analyzed by electrophoresis on a Visible Genetics LONG READ TOWER™ instrument. Sequence analysis of the second template showed 100% match between template 2 and known comparators for human MHC gene HLA DRB1, thus confirming the capacity of the reaction to generate sequencing fragments for two independent species in the same tube.

EXAMPLE 5

In the CLIP reaction, a DNA template is combined with both chain terminating and normal nucleotide triphosphates and processed through multiple chain extension cycles. The reaction is biphasic, however, with an early phase in which extension to full length products is favored, and a later phase in which predominantly chain termination fragments are formed. To illustrate the biphasic nature of the CLIP reaction, a CLIP reaction was performed using a labeled forward primer and an unlabeled reverse primer and aliquots were taken at intervals. FIGS. 7A-D show selected portions of raw data traces for aliquots of sample taken from the CLIP reaction after 8, 17, 26 and 35 cycles.

Figure 8:
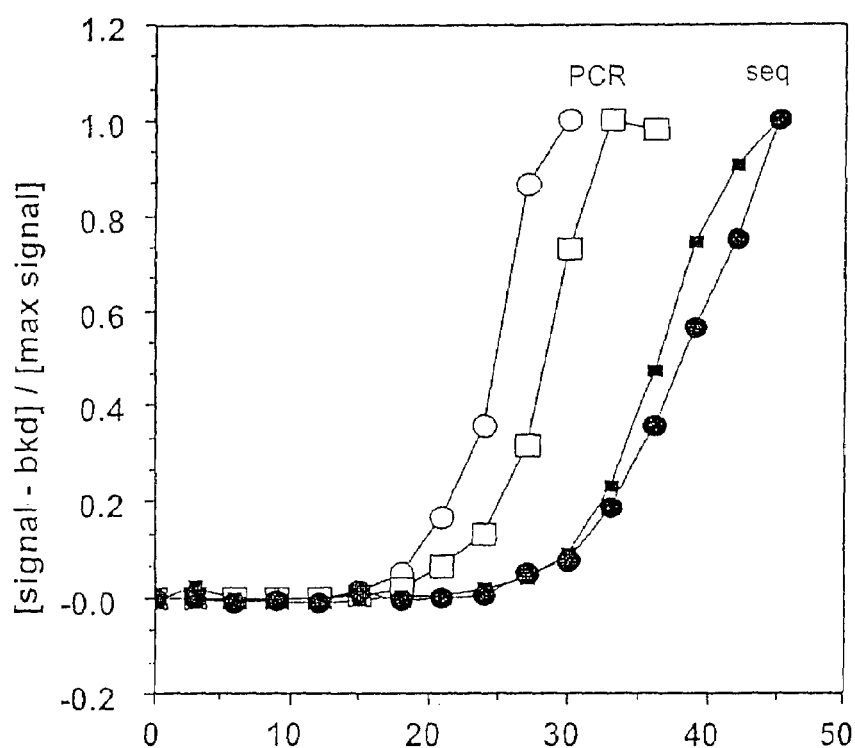
FIG. 8 shows normalized signal intensity as a function of cycle number.

A similar experiment was performed using two labeled primers. FIG. 8 shows a plot of normalized signal intensity as a function of cycle number. The open symbols in FIG. 8 are representative of the full length product, while the closed symbols are representative of the chain-terminated sequencing fragments.

The above experiments clearly confirm the biphasic time-course of the CLIP reaction. Over the first ~20 cycles, the full-length product becomes visible, but very little sequence ladder (chain termination product) is observed. In contrast, over subsequent cycles, the amount of full-length product reaches a plateau and the quantity of dideoxy-terminated sequencing fragments begins to increase. This biphasic behavior can be exploited to simplify the simultaneous determination of the sequence and quantity of a target polynucleotide using the same reagents by taking a measurement for quantitation during the early phase and performing the sequencing analysis on products from the later phase. This can be accomplished by preparing either a single sample or parallel replicate samples. An aliquot is taken out for quantitation after ~20-25 cycles and stored on ice. The other (or remaining) sample is cycled for an additional number of cycles, and a second aliquot is collected after ~26-35 cycles for sequences analysis. The two aliquots are then run on adjacent lanes of a gel for simultaneous sequence determination and quantitation of the amount of the target nucleic acid.

EXAMPLE 6

Figure 9:
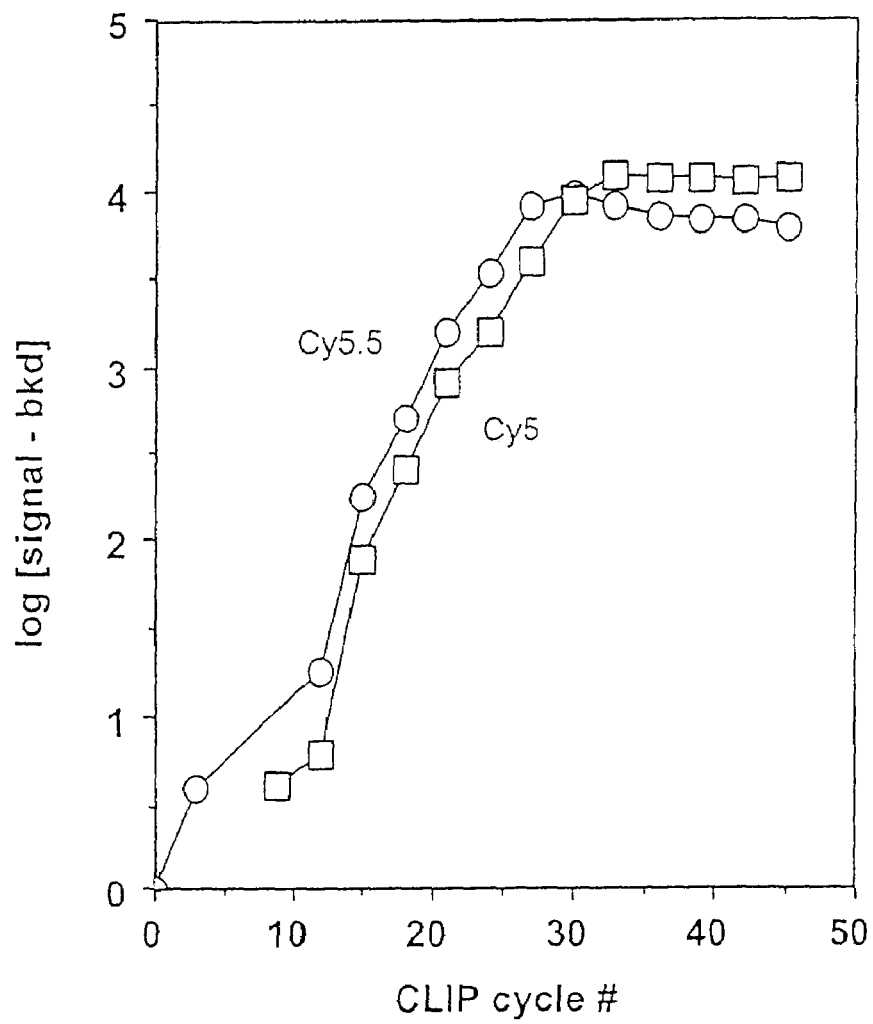
FIG. 9 illustrates the relationship between signal intensity and cycle number in the early phase of the CLIP reaction.

In order to use the CLIP reaction in the method of the invention, it was established that the amount of full-length product increases monotonically with (1) the number of reaction cycles and (2) the amount of template initially present. Only if these two conditions are met, can a meaningful calibration curve be constructed to permit determination of the amount of target nucleic acid in an unknown sample. FIG. 9 illustrates the relationship between signal intensity and cycle number in the early phase of the CLIP reaction. In this experiment, both the forward and reverse primer were labeled and the intensity of the peak associated with the full-length product was measured. FIG. 9 shows that the log of the signal intensity increases monotonically with the number of reaction cycles over a 3 to 4 order of magnitude dynamic range.

Figure 10:
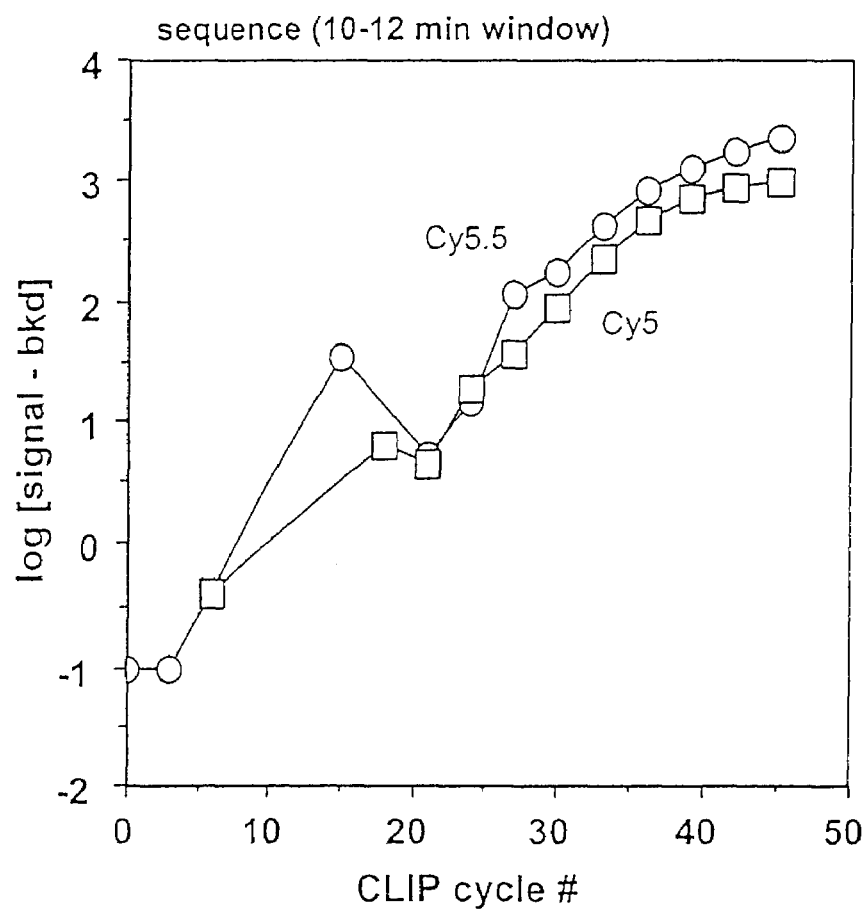
FIG. 10 illustrates the relationship between signal intensity and cycle number in the later phase of the CLIP reaction.

FIG. 10 shows a comparable plot to FIG. 9, but based on the intensity of sequencing fragment peaks obtained in the second phase of the CLIP reaction. Again, the signal intensity increases monotonically with number of cycles over a 3 order of magnitude dynamic range. Thus, in an assay performed without an internal standard, the quantitative result obtained from consideration of the intensity of the full length peak appearing during the early phase of the CLIP reaction can be confirmed by consideration of the intensity of the sequencing ladder peaks appearing during the later phase of the CLIP reaction.

EXAMPLE 7

Template one (the test nucleic acid) is a sequence of HIV-1, M group, B subtype. Template two is another HIV-1 M group template used as the internal quantitation standard. A known amount of template two is added to the test sample, before proceeding with RT-PCR and CLIP. The two templates are simultaneously co-amplified, using an RT-PCR procedure. For the CLIP sequencing, template one is sequenced using P1, a CY 5.0 labeled forward primer, and P2, a Cy 5.5 labeled reverse primer. Template two is sequenced using P3, a Cy 7.0 labeled forward primer, and P4, an unlabelled reverse primer. The template one fragment defined by the primers P1 and P2 is the same size, and approximately the same composition and sequence, as the template two fragment defined by the primers P3 and P4. The forward primers P1 and P3 are identical in length. However, P1 and P3 differ from each other only by the three nucleotides at the 3' end of the oligonucleotide primer. Thus, the two forward primers P1 and P3, although identical in length, and similar in AT content and Tm, only function as sequencing primers for their designated templates, i.e. template one and two respectively. Similarly, the reverse primers P2 and P4 are identical in length, but again differ in the three nucleotides at the 3' end of the oligonucleotide primer. Once again, this results in similar overall AT content and Tm, but the reverse primers P2 and P4 are template specific. Both templates are amplified and sequenced in one CLIP reaction, using AmpliTaq FS polymerase, terminating dideoxynucleoside triphosphates and non-terminating deoxynucleoside triphosphates, and cycled through multiple thermal cycles. The reaction products are analyzed using a Visible Genetics Long Read Tower system, to determine both the sequence and the quantity of template one, using template two as the internal standard for quantitation.

What is claimed is:

1. A method for sequencing and quantitation of a target nucleic acid analyte in a sample, comprising the steps of:
   (a) generating a set of nucleic acid sequencing fragments by processing one or more aliquots of the sample using a set of reagents containing a set of forward and reverse sequencing primers that flank a region of interest of the target nucleic acid between the primers, wherein the primers are sufficiently complementary to the respective 5' ends of the sense and anti-sense strands of the target nucleic acid to produce through a plurality of thermocycles a mixture of primer extension nucleic acid sequencing fragments terminating at each of a particular base type within the target nucleic acid and incorporating a detectable label indicative of the terminating base type that is capable of detection to determine the sequence of the nucleic acid and to determine the amount of target nucleic acid present in the sample, said processing being carried out within a quantitative regime wherein the plurality of thermocycles is performed at cycle numbers where a plot of log of the amount of product as a function of cycle number is linear;
   (b) determining the sequence of the target nucleic acid analyte by separating the labeled nucleic acid sequencing fragments in the modified sample in order of size and detecting the order of separation of the labels associated with the separated sequencing fragments generated in (a); and
   (c) determining the quantity of the target nucleic acid analyte present in the sample by correlating the intensity of a signal obtained from the label of one or more of the sequencing fragments generated in (a) with the amount of the target nucleic acid analyte present in the sample, using a reference standard,
   wherein the sequencing fragments used to determine the sequence of the target nucleic acid and the sequencing fragments used to determine the quantity of target polynucleotide are produced using primers having the same nucleic acid sequence.

2. The method of claim 1, wherein the label of the terminated sequencing fragments is detected and quantitated for the determination of both sequence information about the target nucleic acid and the amount of target nucleic acid present in the sample.

3. The method of claim 1, wherein a labeled full-length primer extension product is detected and quantitated for determination of the amount of target nucleic acid present in the sample.

4. The method of claim 3, wherein the sample is processed in two parallel replicate reactions to produce both full-length product and terminated polynucleotide sequencing fragments, said two reactions including a first reaction which is stopped after a first number of thermal cycles such that the production of full-length product is within a quantitative regime, and a second reaction which is stopped after a second number of thermal cycles greater than the first number of thermal cycles such that the production of sequencing fragments is within a quantitative regime.

5. The method of claim 3, wherein the sample is processed in a single reaction and a first aliquot of the single reaction is removed after a first number of thermal cycles such that the production of full-length product is within a quantitative regime, said full length-product in the first aliquot being used for determination of the amount of target nucleic acid in the sample, and wherein the sample is further processed after the removal of the first aliquot for an additional number of thermal cycles such that production of sequencing fragments is within a quantitative regime.

6. The method of claim 3, wherein an internal polynucleotide reference standard is added to the sample in a known amount and coprocessed in the same reaction vessel to produce a detectable reference product, and wherein the intensity of a signal derived from the reference product is compared to the intensity of the signal derived from the label associated with the separated fragments to determine the quantity of the target nucleic acid analyte in the sample.

7. The method of claim 6, wherein the target nucleic acid is an RNA target, and wherein the method further comprises the step of reverse transcribing the RNA target to produce a cDNA template prior to step (a).

8. The method of claim 1, wherein an internal polynucleotide reference standard is added to the sample in a known amount and coprocessed in the same reaction vessel to produce a detectable reference product, and wherein the intensity of a signal derived from the reference product is compared to the intensity of the signal derived from the label associated with the separated fragments to determine the quantity of the target nucleic acid analyte in the sample.

9. The method of claim 8, wherein the target nucleic acid is an RNA target, and wherein the method further comprises the step of reverse transcribing the RNA target to produce a cDNA template prior to step (a).

10. The method of claim 8, wherein the label of the terminated sequencing fragments is detected and quantitated for the determination of both sequence information about the target nucleic acid and the amount of target nucleic acid present in the sample.

11. The method of claim 1, wherein both a labeled full-length product and labeled terminated sequencing fragments are detected and quantitated for the determination of the amount of target nucleic acid present in the sample.

12. The method of claim 1, wherein the target nucleic acid is an RNA target, and wherein the method further comprises the step of reverse transcribing the RNA target to produce a cDNA template prior to step (a).

13. The method of claim 12, wherein the target nucleic acid analyte is HIV-1, and wherein the set of reagents includes primers flanking a region of interest within the HIV-1 genome.

14. The method of claim 13, wherein an internal polynucleotide reference standard is added to the sample in a known amount and coprocessed in the same reaction vessel to produce a detectable reference product, and wherein the intensity of a signal derived from the reference product is compared to the intensity of the signal derived from the label associated with the separated fragments to determine the quantity of the target nucleic acid analyte in the sample.

* * * * *